United States Patent [19]

DiGiacomo et al.

[11] 4,276,410

[45] Jun. 30, 1981

[54] LAYERED ORGANOPHOSPHORUS INORGANIC POLYMERS CONTAINING MERCAPTO OR THIO GROUPS

[75] Inventors: Peter M. DiGiacomo, Mission Viejo; Martin B. Dines, Santa Ana, both of Calif.

[73] Assignee: Occidental Research Corporation, Irvine, Calif.

[21] Appl. No.: 54,097

[22] Filed: Jul. 2, 1979

[51] Int. Cl.$^3$ .................. C08G 67/00; C08G 75/00; C08G 79/04

[52] U.S. Cl. .................. 528/373; 260/429.1; 260/429.2; 260/429.3; 260/429.5; 260/435 R; 528/374; 528/395

[58] Field of Search .................. 528/373, 374, 395

[56] References Cited

U.S. PATENT DOCUMENTS

| 3,654,189 | 4/1972 | Venezky | 528/9 |
| 4,026,830 | 5/1977 | Gillman et al. | 528/395 |

Primary Examiner—Wilbert J. Briggs, Sr.
Attorney, Agent, or Firm—Christie, Parker & Hale

[57] ABSTRACT

Sulfur-containing organophosphorus acid compounds react by a metathesis reaction in a liquid medium with tetravalent metal ions yielding layered crystalline to amorphous inorganic polymers having the empirical formula $M(O_3PRSH)_2$, or $M(O_3PRSR')_2$ where M is a tetravalent metal and R and R' are organic groups covalently bonded to phosphorus and the sulfur-containing group. One use for the compounds is as ion complexers.

12 Claims, 11 Drawing Figures

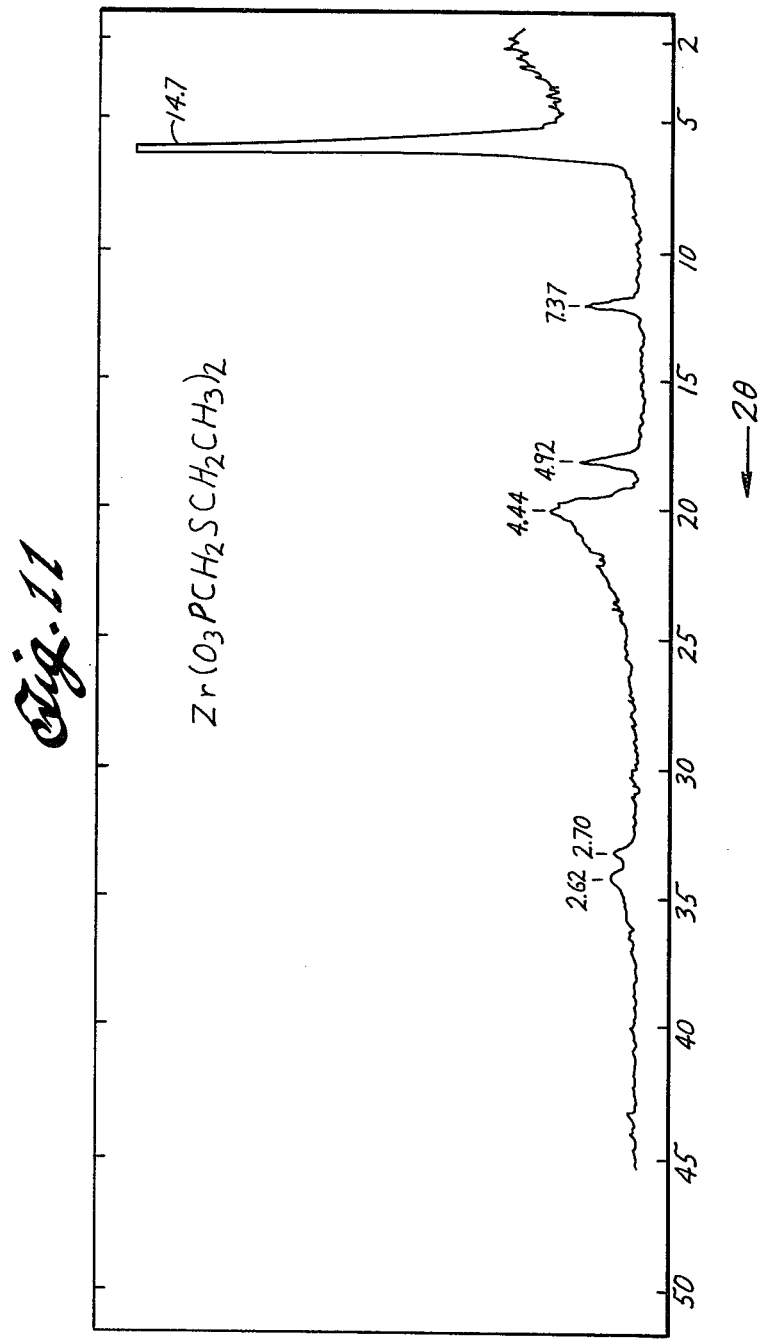

LAYERED ORGANOPHOSPHORUS INORGANIC POLYMERS CONTAINING MERCAPTO OR THIO GROUPS

BACKGROUND OF THE INVENTION

This application is related to applications Ser. No. 945,971, filed Sept. 26, 1978, now U.S. Pat. No. 4,232,146, issued Nov. 4, 1980 and titled "Process for Preparing Layered Organophosphorus Inorganic Polymers," Ser. No. 952,228, filed on Oct. 17, 1978, now U.S. Pat. No. 4,235,990, issued on Nov. 25, 1980 and titled "Layered Carboxy End Terminated Organophosphorus Inorganic Polymers," Ser. No. 966,197 filed Dec. 4, 1978, now U.S. Pat. No. 4,235,991, issued Nov. 25, 1980 and titled "Layered Sulfonate End Terminated Organophosphorus Inorganic Polymers," Ser. No. 7,275, filed Jan. 29, 1979 and titled "Layered Zirconium Bis(benzenephosphonate) Inorganic Polymers", Ser. No. 43,810 filed May 30, 1979 and titled "Process for Preparing Organophosphorous Inorganic Polymers," and Ser. No. 54,107 filed concurrently with this application and titled "Layered Cyano End Terminated Organophosphorus Inorganic Polymers," the entire disclosures of which are incorporated herein by this reference.

The present invention is directed to solid inorganic polymers having sulfur-containing groups anchored to the surfaces of the polymers. The polymers formed can be layered crystals which display intercalation activity, or they can be partially or totally amorphous.

The interface surfaces of solids are responsive regions of chemical and physical action. Many practical chemical and physical phenomena such as absorption, corrosion, inhibition, heterogeneous catalysis, lubrication, ion exchange activity, adhesion and wetting and electrochemical activity occur on or as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in the active sites which arises from the nature of their surface structure. Furthermore, much of the active sites are usually buried within the surface, and as a result of these two factors, elevated temperature and low conversions are typically required to make a process effective. Exceptions in which homogeneous agents have been used include the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the nonuniform situation of sites which has manifested itself in loss of expected selectivity, activity and even in attrition.

Many inorganic solids crystallize with a layered structure and present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "intercalation," the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, the potential surface is greater than the actual surface by a factor of the number of lamella composing the crystal. This value is typically on the order of $10^2$–$10^4$. Although edge surface is practically insignificant compared to basal surface, it is critical to the rate of intercalation, since the inclusion process always occurs via the edges. This is because bonding within the sheets is strong, and therefore, penetration of the sheets is an unlikely route into the crystal.

Previous studies of the intercalative behavior of layered compounds have mainly been conducted by solid state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process and on deintercalation the guests undergo only minor perturbation.

In order for a more active process to occur during intercalation, such as selective fixation or catalytic conversion, specific groups must be present which effect such activity. There might also be some preferable geometric environment about each site, as well as some optimal site-to-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis," Boersma, Academic Press, N.Y. (1977), Burton et al., editors, and "Catalysis in Organic Chemistry," Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ionic or van der Waals forces of intercalated guests were operating.

One of the few layered compounds which have available sites is zirconium phosphate $Zr(O_3POH)_2$. It exists in both amorphous and crystalline forms which are known to be layered. In the layered structure, the site-site placement on the internal surfaces is about 5.3, which leads to an estimated $25^2$ area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and nontoxic.

Quite a bit of work has been conducted on the zirconium phosphate, mainly because it has been found to be a promising inorganic cation hanger for alkali, ammonium and actinide ions, see Alberti, "Accounts of Chemistry Res." 11, 163, 1978, incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and the Michel and Weiss, "Z. Natur," 20, 1307 (1965) both incorporated herein by reference. A. Yamaka described the reaction of this solid with ethylene oxide, which does not simply incorporate between the layers as do the other organics, but rather was found to irreversibly react with the acidic hydroxyls to form a covalent bonded product, Yamaka, "Inorg. Chem." 15, 28-1, (1976). This product is composed of a bilayer of anchored ethonolic groups aimed into interlayers. The initial layer-layer repeat distance is expanded from about 7.5 to 15 A, consistent with the double layer of organics present. The overall consequence of this reaction is to convert inorganic acid hydroxyls to bound organic alkanol groups. This conversion, while of interest, has limited if any improvement over the hydroxyls already available on zirconium phosphate.

A very recently reported effort in the field is Alberti, et al., "J. Inorg. Nucl. Chem.," 40, 1113 (1978) which is incorporated herein by reference. A method similar to that of this invention for the preparation of zirconium bis(benzenephosphonate), zirconium bis(hydroxymethanephosphonate) monohydrate, and zirconium bis(-monoethylphosphate) is described, with descriptions of the properties for these products.

SUMMARY OF INVENTION

According to the present invention there is provided inorganic polymers having sulfur-containing groups pendant to phosphorus atoms wherein the phosphorus atoms are, in turn, linked by oxygen to tetravalent metal atoms. The pendant sulfur containing groups are coupled to phosphorus directly or through an organic group.

Compounds provided in accordance with the invention are inorganic polymers providing pendant sulfur-containing groups and which include units of the formula:

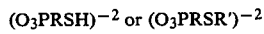

wherein R and R' are organo groups, in which the phosphorus is structurally linked through each of the available oxygens to a tetravalent metal selected from the group consisting of zirconium, cerium, thorium, uranium, hafnium, lead, titanium, and mixtures thereof and wherein the molar ratio of phosphorus to tetravalent metal in said inorganic polymer is about 2 to 1.

Units of sulfur-containing phosphorus acid homopolymers which are inorganic phosphonate polymers have the empirical formula:

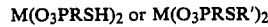

wherein R and R' are as defined above and M is a tetravalent metal.

The compounds of the invention are formed by a liquid media reaction in which at least one sulfur-containing phosphorus acid compound of the formula:

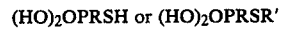

wherein R and R' are as defined above, is reacted with at least one tetravalent metal ion selected from the group consisting of zirconium, cerium, thorium, uranium, lead, hafnium, titanium and mixtures thereof. The molar ratio of phosphorus to the tetravalent metal in the product is 2 to 1. Reaction, however, preferably occurs in the presence of an excess of phosphorus containing acid reactants to consume all of the metal ions and the metal ion is provided as a compound soluble in the liquid media.

Introduction of the sulfur group may be carried out before or after formation of the organophosphorus inorganic polymer, resulting in different degrees of crystallinity.

Other organophosphorus acid compounds may be present for reaction to form part of the inorganic polymer which is the product of the reaction. These organophosphorus acid compounds need not contain sulfur-containing functions. They may contain substituents which have functional groups that interact with the sulfur-containing groups in the product. Donor functional groups such as sulfonate, nitrile, ether, ester, amide, oxo, carboxy, hydroxy, and the like influence the ion binding activity of sulfur-containing groups. These substituents may also contain ionic groups. These ionic groups would modify the activity of the sulfur-containing group. Phosphoric and/or phosphorous acid can also be present as reactive dilutants.

The products formed are layered crystalline to semi-crystalline to amorphous in nature. The pendant sulfur-containing groups serve as ion exchangers, as intermediates for the addition or substitution of other functional groups, and as metal catalyst supports.

Multicomponent polymers, containing other organic groups interspersed with the sulfur-containing group, can be prepared. In addition, a mixture of two or more sulfur-containing acids can be used in the preparation.

THE DRAWINGS

Figure 1:
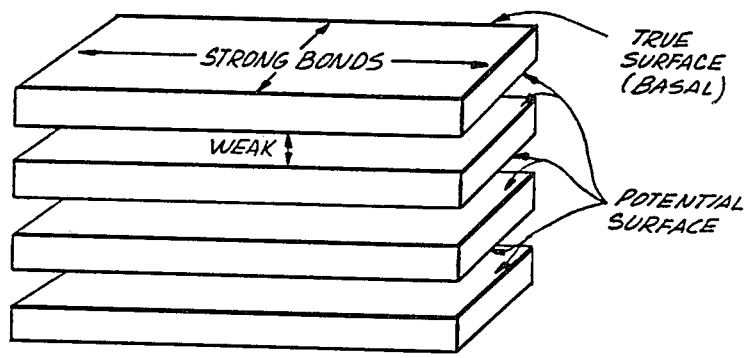
FIG. 1 illustrates a layered microcrystal. Each lamellar slab is formed of strong covalent bonds and has a thickness of about 10 atoms.
Figure 2:
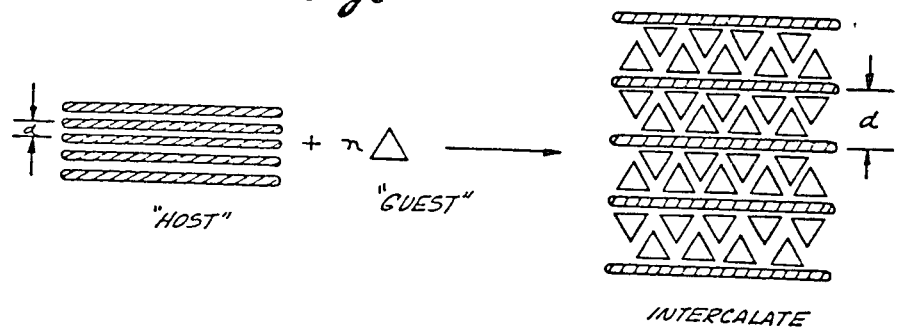
FIG. 2 illustrates intercalation where the interlayer distance is shown as "d."
Figure 3:
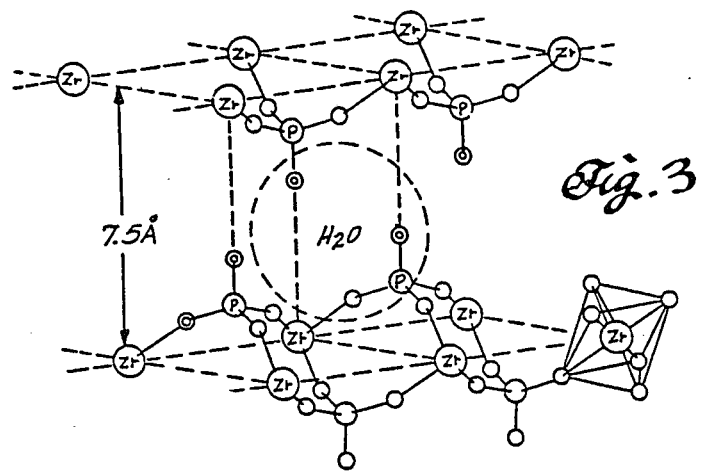

FIG. 3 illustrates the accepted structure for zirconium phosphate and spacing between layers. The dashed lines between zirconium (Zr) atoms is to establish the plane between them. In the drawing P=Phosphorus, O=Oxygen and water of hydration is shown.

Figure 4:
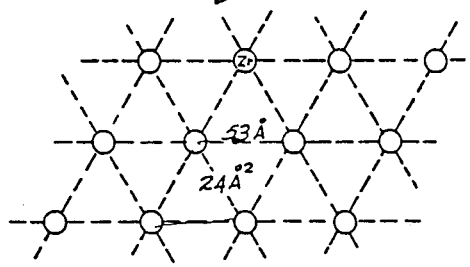

FIG. 4 illustrates a projection of the zirconium plane showing accepted spacing between Zr atoms and the available linkage area.

Figure 5:
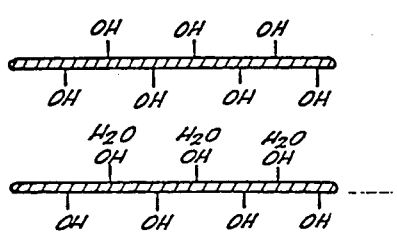

FIG. 5 is a symbolized depiction of spaced zirconium phosphate layers showing covalently bonded hydroxyl groups and water of hydration.

Figure 6:
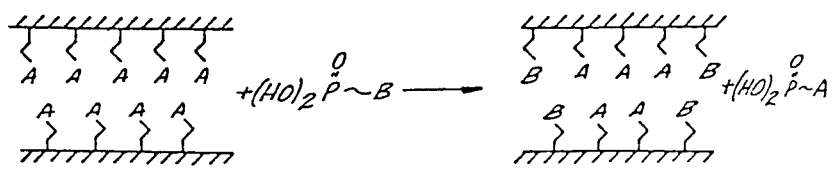

FIG. 6 illustrates an exchange reaction where anchored sulfur-containing groups ("A") are to be substituted by "B," and represents the portion of the organo group linking the terminal group "A" or "B" to the crystals or the organophosphorus acid compound reactant.

Figure 7:
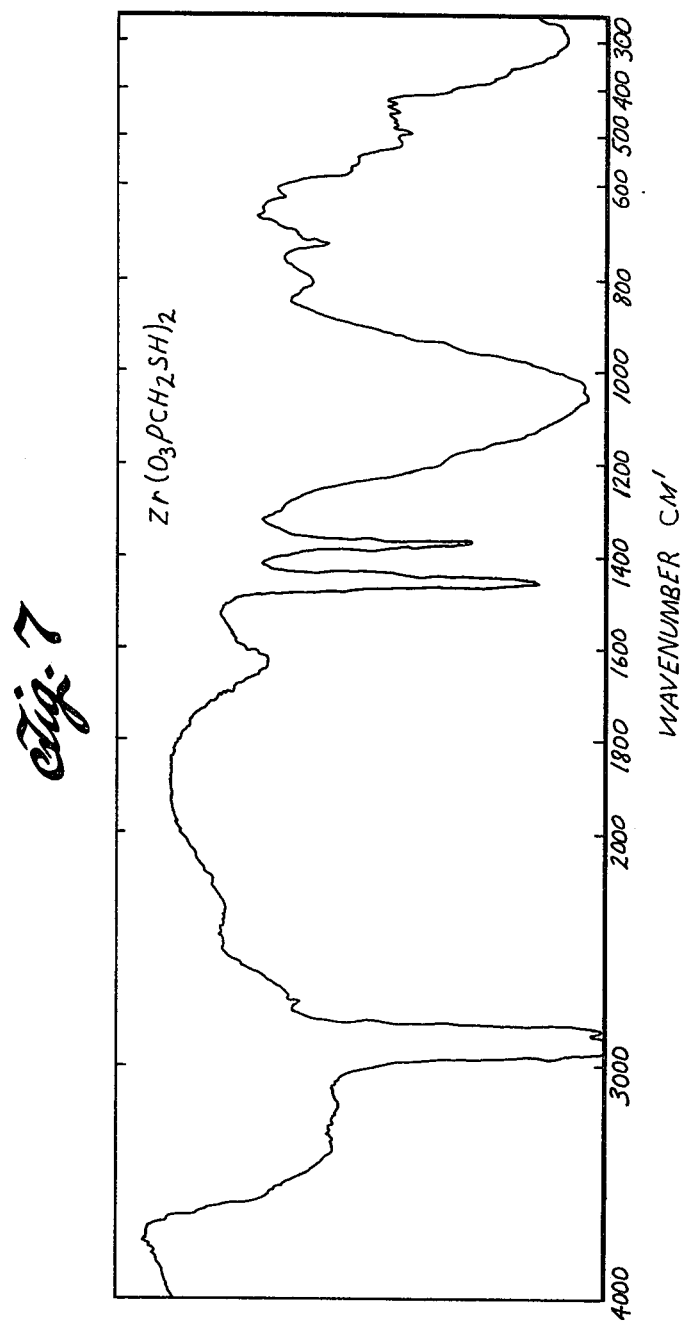

FIG. 7 is an infrared absorption spectrum of zirconium bis(mercaptomethylphosphonate), as prepared in Example 1.

Figure 8:
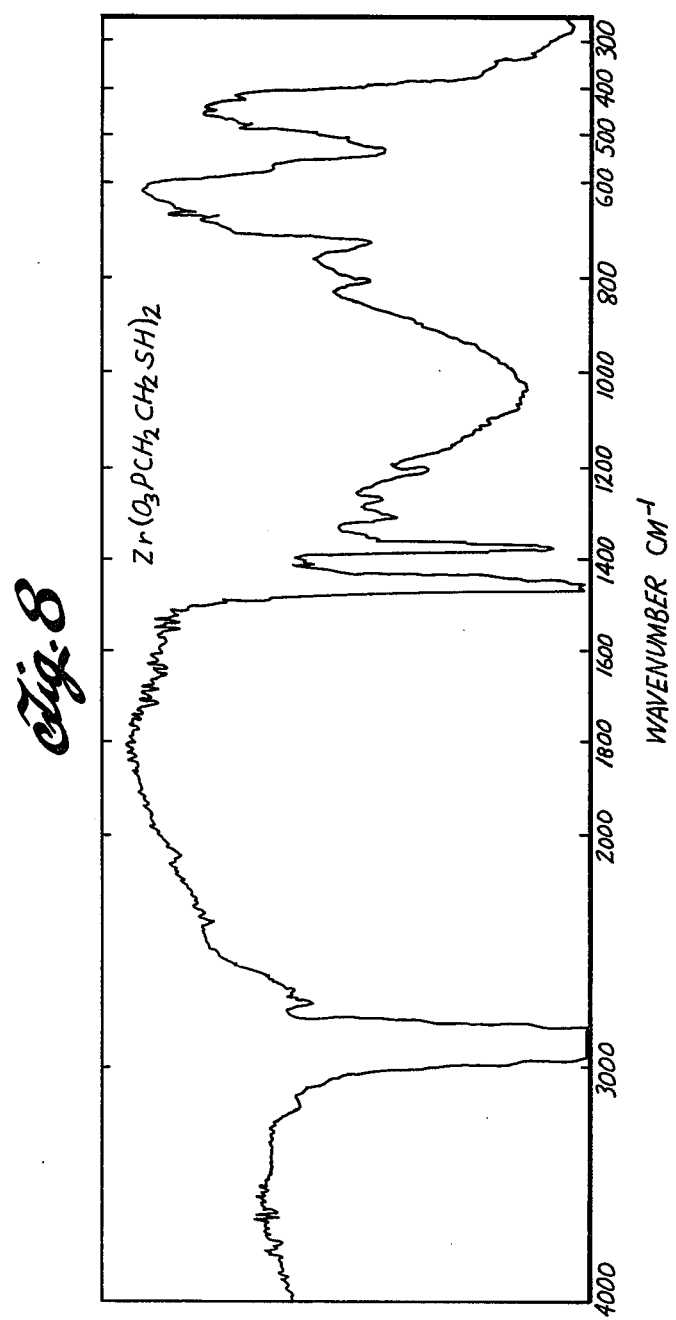

FIG. 8 is the infrared absorption spectrum for zirconium bis (2-mercaptoethylphosphonate), as prepared in Example 2.

Figure 9:
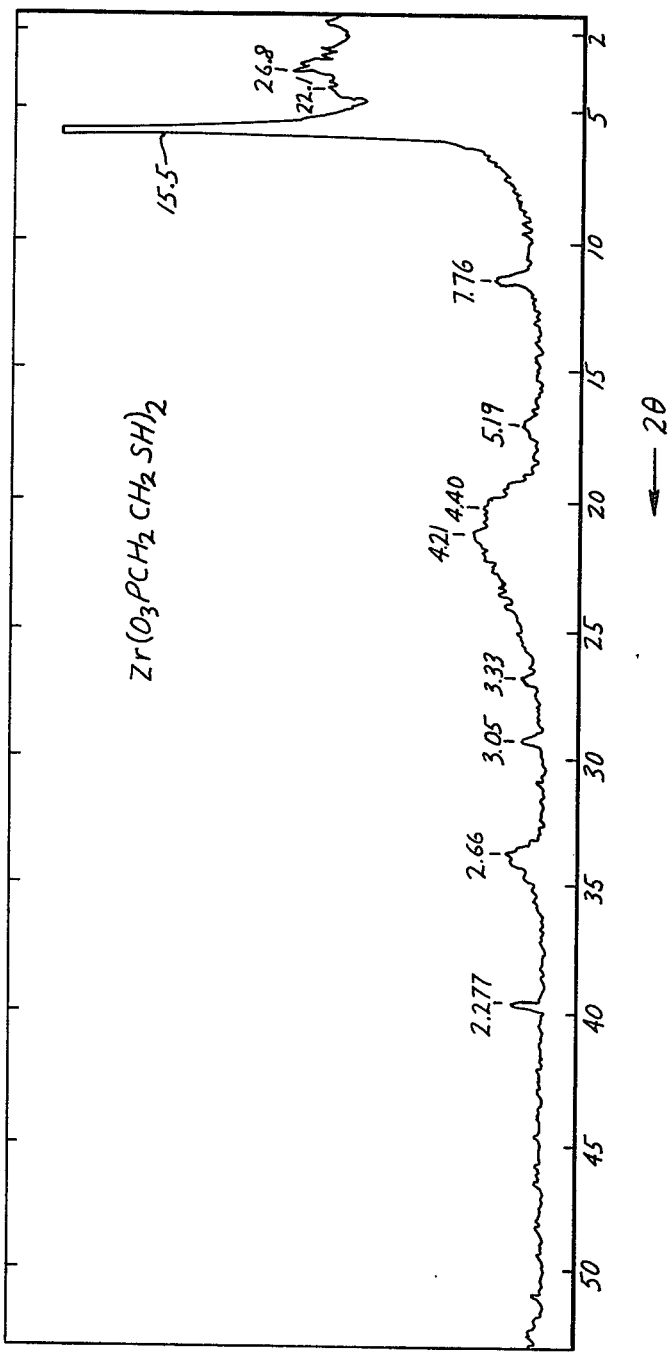

FIG. 9 is an X-ray powder diffraction pattern for the compound prepared in Example 2.

Figure 10:
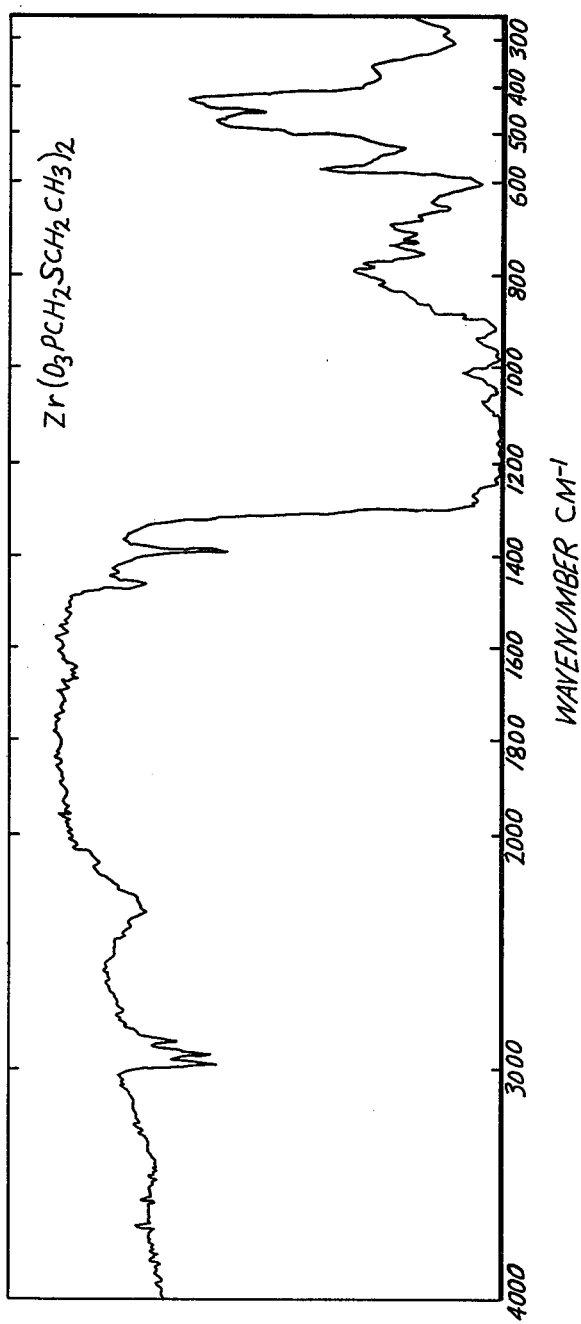

FIG. 10 is the infrared absorption spectrum of zirconium bis(ethylthiomethylphosphonate), prepared in Example 3.

FIG. 11 is an X-ray powder diffraction pattern for the compound prepared in Example 3.

DETAILED DESCRIPTION

According to the present invention, there is provided crystalline to amorphous inorganic polymers formed of structural units of the formula:

$$M(O_3PRSH)_2 \text{ or } M(O_3PRSR')_2$$

wherein R and R' are organo groups, R covalently bonds the sulfur-containing group to phosphorus and wherein each phosphorus is linked through oxygen to a tetravalent metal selected from the group consisting of zirconium, cerium, thorium, uranium, lead, titanium, hafnium, and mixtures thereof and wherein the molar ratio of phosphorus to tetravalent metal in said inorganic polymer is about 2 to 1.

Homopolymers are where inorganic phosphonate polymers have the empirical formula:

$$M(O_3PRSH)_2 \text{ or } M(_3PRSR')_2$$

wherein R and R' are as defined as above, with R linked to phosphorus by carbon, and M is a tetravalent metal ion selected from the group consisting of zirconium, cerium, thorium, uranium, lead, titanium, hafnium and mixtures thereof. Typically, R contains from 1 to about 17 carbon atoms, preferably from 1 to 8 carbon atoms.

The polymers are prepared by a liquid phase methathesis reaction of at least one sulfur-containing phosphorus acid compound having the formula:

$$(HO)_2OPRSH \text{ or } (HO)_2OPRSR'$$

wherein R and R' are as defined above, with at least one tetravalent metal ion selected from the group consisting of zirconium, thorium, cerium, uranium, hafnium, lead, titanium and mixtures thereof to form a solid inorganic polymer precipitate in which phosphorus is linked to the metal by oxygen and the sulfur-containing organo group is covalently bonded to the phosphorus atoms. The sulfur-containing group is pendent from the inorganic polymer. Typically, the tetravalent metal ion is provided as a soluble salt MX wherein M is tetravalent metal as defined above and X is the anion(s) of the salt. Typical anions include halides such as $Cl^-$, $HSO_4^{-2}$, $O_2C\text{-}CH_3^{-1}$, $O^{-2}$ and the like.

The polymeric reaction products formed have been found to be layered crystalline or semi-crystalline in nature and, as such, provide layered structures similar to zirconium phosphate. The amorphous portion of polymers possess a large quantity of available pendent groups and is similar to silica gel.

By the term "sulfur-containing phosphorus acid compound," as used herein, there is meant a compound of the formula:

$$(HO)_2OPRSH, \text{ or } (HO)_2OPRSR'$$

wherein RSH or RSR', is any organo group which will replace an hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is preferred with coupling through carbon particularly preferred.

By the term "organophosphorus acid compound" as used herein, there is meant compounds other than sulfur-containing compounds having the formula:

$$[(HO)_2OP]_xR'' \text{ herein x is 1 or 2}$$

and R'' is an organo group other than one providing the sulfur as mercapto or thio groups. Coupling is preferably through carbon or an oxygen-carbon group and may be used as indicated below as co-reactants or as exchange reactants.

When coupling is through carbon, the sulfur-containing phosphorus acid compound or the organophosphorus acid compound is a sulfur-containing or organo phosphonic acid and the product is a phosphonate. When coupling is through oxygen-carbon, the sulfur-containing phosphorus acid compound or organosphosphorus acid compound is sulfur-containing or organo phosphoric monoester acid and the product is a phosphate.

The general reaction for mercapto phosphonic acids alone is shown in equation (1) below and for monoesters of phosphoric acid alone by equation (2).

$$M^{+4} + 2(HO)_2OPRSH \rightarrow M(O_3PRSH)_2 \quad (1)$$

$$M^{+4} + 2(HO)_2OPOR'''SH \rightarrow M(O_3P(OR'''SH)_2 \quad (2)$$

wherein R''' is the remainder of the organo group "R."

The product contains phosphorus to metal in a molar ratio of about 2 to 1, and the empirical formula for the product would show all groups bound to phosphorus.

In general, the choice of R will affect compound stability, the acidity of the mercapto or thio group, the hydrophilic-hydrophobic nature of the solid, interlamellar spacing, crystal size, etc.

While nowise limiting, the R groups attachable may be saturated or unsaturated, substituted and unsubstituted and include, among others, alkyl, alkylene, alkyne, aryl, alkylaryl, heterocyclics and the like or can be partially or wholly halogen substituted, e.g., perfluoroalkyl. Typically, the group will contain from about 1 to about 17 carbon atoms, preferably from 1 to about 8 carbon atoms.

While nowise limiting, the R' groups attachable to organophosphorus acid compounds may be saturated and unsaturated, substituted and unsubstituted and include among others, alkylene, alkyloxy, alkyne, aryl, haloalkyl, alkylaryl, aryloxy, aminoalkyl, morpholinoalkyl, sulfoalkyl, phenoxyalkyl, beta-diketo alkyl, alkyl, cyanoalkyl, cyanoalkoxy, heterocyclics and the like or can be partially or wholly halogen substituted.

In general, the organo group should occupy no more than about 25 Å$^2$ for proper spacing. This limitation is imposed by the basic crystal structure of zirconium phosphate. Referring to FIG. 4, a spacing of 5.3 Å is shown between zirconium atoms in the zirconium plane of a crystal, a total area of about 24 Å$^2$ is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than 25 Å$^2$, adjacent groups may be somewhat larger than 25 Å$^2$ and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE 1

| Moiety | Minimum Area (A$^2$) | Moiety | Minimum Area (A$^2$) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromethyl | 17 |
| Nitrile | 9 | Diphenylphosphine | 50 (approx.) |
| Morpholino | 21 | Mercaptoethyl | 13.5 |
| Trimethylamino | 25 | | |

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the sulfur-containing and organophosphorus acid compounds are hygroscopic, an organic solvent such as ethanol may be employed, where water interferes with the reaction or where solubility is to be promoted. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the sulfur-containing phosphorus acid compound may serve as a solvent. Typically, the liquid medium is the liquid medium in which the sulfur-containing acid compound is formed.

For complete consumption of the tetravalent compound, the amount of acid employed should be sufficient to provide two moles of phosphorus per mole of tetravalent metal. An excess is preferred. Phosphorous acid and/or phosphoric acid, if present, will enter into the reaction and provide an inorganic polymer diluted in respect to the sulfur-containing groups in proportion to the amount of phosphorous or phosphoric acid employed.

Reaction is virtually instantaneous at all temperatures leading to precipitation of layered crystalline and semi-crystalline inorganic polymer solids.

An amorphous phase may appear as a gel similar to silica gel. The gel can be crystallized by extended reflux in the reaction medium, usually from about 5 to 15 hours. The semi-crystalline product is characterized by a rather broad X-ray powder pattern.

The presence of sequestering agents for the metal ion slows down the reaction and also leads to more highly crystalline products. For instance, hydrogen fluoride is a sequestering agent for zirconium and nitrate ion a sequestering agent for thorium. Both slow the reaction and promote the information of highly crystalline end products.

As compared to zirconium phosphate forming crystals of 1-5 microns, crystals of 100 to 1000 microns in size have been prepared.

The process of preparation permits a wide variety of inorganic polymers to be formed having the characteristics of the organo group protected by the inorganic polymer structure and with subsequent exchange or substitution reactions, the formation of other inorganic polymers. Polymers formed may be block, random and the like.

For instance, a mixture of sulfur-containing phosphorus acid compounds, mixtures of sulfur-containing and organo-phosphorus acids and organo-phosphorus acid compounds may be reacted with one or more of the tetravalent metal ions. If phosphorous and/or phosphoric acid is present, it will enter into the reaction as a reaction diluent.

The high surface area of the crystalline products also make them useful for sorption of impurities from aqueous and non-aqueous media.

Another utility is as an additive to polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals; substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from laboratory chemical suppliers. The products formed are insoluble in normal solvents and do not sublime. However, the combined weight of yield data, spectroscopy and powder diffraction results confirm the compositions reported with good reliability.

X-ray powder patterns were run on a Phillips diffractometer using CuK radiation. Infrared spectra were obtained with a Beckman spectrophotometer.

EXAMPLE 1

A 15.895 g charge of 85% chloromethylphosphonic acid was reacted ith 8.308 g of sodium hydroxide to form the sodium salt of the acid. Following this, 53.758 g of thiourea (about seven times the stoichiometric requirement) was added, along with sufficient deionized water to make a total volume of about 200 ml. The mixture was heated to boiling and permitted to reflux overnight, during which time the volume was reduced to about 70 ml.

The reaction mixture was added, with stirring, to about 250 ml of ethanol, precipitating the reaction product, $Na_2PO_3CH_2SC(NH_2)_2+cl^-$, which was isolated by filtration.

An equivalent of sodium hydroxide (assuming a total reaction), 8.286 g, was reacted with the reaction product in aqueous solution, the mixture was heated and evaporated to about 50 ml, and then about 250 ml of ethanol was added. A greenish oil formed.

After separting the layers, the oil was treated with 30.6 g of concentrated hydrochloric acid to form mercaptomethylphosphonic acid. Some hydrogen sulfide was also released.

Upon the addition of 6.269 g of zirconyl chloride octahydrate, a precipitate formed almost immediately. The slurry was heated and refluxed overnight.

The solid was separated by filtration, then washed successively with deionized water, acetone and ethyl ether. After drying several hours at about 70° C., the yield was 7.249 g, which is 98.3% of theoretical for the formation of zirconium bis(mercaptomethylphosphonate) dihyrate.

Elemental analysis of the compound gave the following composition: 7.43% C, 2.65%H and 12.37%S. An infrared absorption spectrum was taken, and is shown as FIG. 7. The X-ray powder diffraction pattern shows the compound to be amorphous to semicrystalline.

EXAMPLE 2

A 10 ml portion of freshly distilled thioacetic acid was placed in a glass tube, previously closed on one end. To this was added, with mixing, 7.798 g of diethylvinylphosphonate and the open end of the tube was sealed.

The glass tube was placed in a glass container and the container was partially filled with isopropanol. The container was inserted into a Parr digestion bomb, the bomb was sealed and, finally, flushed with nitrogen. Isopropanol was used to moderate the temperature of reaction, its boiling point of 82° C. being lower than that of thioacetic acid.

The bomb was heated to 125° C., maintained at that temperature for about four hours and allowed to cool overnight.

After opening the bomb and glass tube, a sample of the reaction mixture was injected into a gas chromatograph. Diethylvinylphosphonate had disappeared from the mixture and a new peak appeared, comprising 55% of the total peak area, which indicates that the reaction was essentially complete, forming diethyl(acetothioethyl) phosphonate. Excess thioacetic acid was evaporated off, using a rotary evaporator, until the gas chromotograph indicated 75% reaction product, about 15% thioacetic acid and no other component greater than 4%. A clear yellow viscous liquid weighing 12.37 g remained.

A 6.76 g portion of the liquid was placed in a flask with 4.41 g of 50% sodium hydroxide solution, then the mixture was refluxed with stirring for about 2.5 hours. About 30 g of 47% hydrobromic acid was added, with refluxing and stirring for another 2 hours, forming 2-mercaptoethylphosphonic acid.

Half of the phosphonic acid product was treated with b 1 g of zirconyl chloride octahydrate, quickly forming a white precipitate. About 2 ml of concentrated hydrofluoric acid was added to dissolve the precipitate and the mixture was heated. As the hydrofluoric acid evaporated, the precipitate slowly reappeared, and the slurry was refluxed for about 24 hours.

The solid material was isolated by filtration, washed with deionized water, washed with methanol, then dried at about 75° C. for several hours. The yield was 1.721 g of yellow solid, zirconium bis(2-mercaptoethylphosphonate).

An infrared absorption spectrum was obtained for the material, and is shown as FIG. 8. Elemental analysis yielded the composition: 17.63%C, 3.70%H and 13.42%S. An X-ray powder diffraction pattern was obtained, and is shown as FIG. 9, with an interlayer spacing of 15.5Å.

EXAMPLE 3

A 4.00 g portion of diethyl(ethylthiomethyl) phosphonate was mixed with 15 ml of 48% hydrobromic acid, and the mixture refluxed for about 30 minutes to form ethylthiomethylphosphonic acid. About 10 ml of deionized water was used to dissolve 1.660 g of zirconyl chloride octahydrate, and this was added to the reaction mixture. A yellow precipitate formed very rapidly.

To improve the crystallinity of the precipitate, 3 ml of 48% hydrofluoric acid was added and refluxing was permitted to continue for another hour, after which the mixture was cooled to room temperature and allowed to stand over a weekend. Following this, the mixture was reheated and refluxed for about 30 minutes.

The solid material was isolated by filtration and washed successively with hot deionized water, ethanol and ethyl ether, then dried at about 100° C. for 1 hour yielding 2.146 g of zirconium bis(ethylthiomethylphosphonate).

Elemental analysis of the product gave the following composition: 17.30%C, 3,89%H, 8.7%F and 15.3%S. An infrared absorption spectrum was obtained and is shown as FIG. 10. The X-ray powder diffraction pattern, FIG. 11, shows an interlayer spacing of 14.7Å.

EXAMPLE 4

In an experiment to determine the ability of zirconium bis(mercaptomethylphosphonate) to extract silver ions from solution, 0.076 g of the compound prepared in Example 1 was shaken in a vial with 5 ml of 0.10 M silver nitrate. The mixture was allowed to stand for several days, after which a sample of the supernatant liquid was decanted for analysis.

The original silver solution contained 10.8 g/l silver and the "extracted" solution was found to contain 4.96 g/l silver, indicating that 5.85 g/l silver was extracted by the compound.

What is claimed is:

1. Inorganic phosphorus containing polymers providing pendant mercapto or thio groups, and which contain units of the formula M(O$_3$PRSH)$_2$, or M(O$_3$PRSR')$_2$ wherein R and R' are organo groups and the oxygen atoms are bonded to phosphorus and structurally linked to M which is one or more tetravalent metals selected from the group consisting of zirconium, cerium, thorium, uranium, hafnium, lead and titanium, and wherein the molar ratio of phosphorus to tetravalent metal in the inorganic phosphorus containing polymer is about 2 to 1.

2. Inorganic phosphorus containing polymers as in claim 1 in which each of the organo groups contains from 1 to about 17 carbon atoms.

3. Inorganic phosphorus containing polymers as in claim 1 in which each of the organo groups contains from 1 to about 8 carbon atoms.

4. Inorganic phosphonate polymers having the empirical formula M(O$_3$PRSH)$_2$ wherein R is an organo group which is bonded to phosphorus through carbon and M is one or more tetravalent metal ions selected from the group consisting of zirconium, cerium, thorium, uranium, hafnium, lead and titanium.

5. Inorganic phosphonate polymers as in claim 4 in which R contains from 1 to about 17 carbon atoms.

6. Inorganic phosphonate polymers as in claim 4 in which R contains from 1 to about 8 carbon atoms.

7. Inorganic phosphonate polymers having the empirical formula M(O$_3$PRSR')$_2$ wherein R and R' are organo groups, R is bonded to phosphorus through carbon and M is one or more tetravalent metal ions selected from the group consisting of zirconium, cerium, thorium, uranium, hafnium, lead and titanium.

8. Inorganic phosphonate polymers as in claim 7 in which each of the organo groups contains from 1 to about 17 carbon atoms.

9. Inorganic phosphonate polymers as in claim 7 in which each of the organo groups contains from 1 to about 8 carbon atoms.

10. Inorganic phosphonate polymers of zirconium bis(mercaptomethylphosphonate).

11. Inorganic phosphonate polymers of zirconium bis(2-mercaptoethylphosphonate).

12. Inorganic phosphonate polymers of zirconium bis(ethylthiomethylphosphonate).

* * * * *

UNITED STATES PATENT AND TRADEMARK OFFICE
CERTIFICATE OF CORRECTION

PATENT NO. : 4,276,410
DATED : June 30, 1981
INVENTOR(S) : Peter M. DiGiacomo
Martin B. Dines It is certified that error appears in the above-identified patent and that said Letters Patent are hereby corrected as shown below:

Column 3, line 20, "11, 163," should read -- $\underline{11}$, 163," --; line 25, "23, 477" should read -- $\underline{23}$, 477" --; line 25, "and the Michel" should read -- and Mic$\overline{\text{he}}$l --; line 26, "20, 1307" should read -- $\underline{20}$, 1307 --; line 32, "15, 28-1," should read -- $\underline{15}$, 28-1,--; line 36, "15 A," should read -- 15$\overset{\circ}{\text{A}}$, --; line 43, "40, 1113" should read -- $\underline{40}$, 1113 --. Column 6, line 39, "organosphosphorus" should read -- organophosphorus --; Column 10, line 12, "b 1 g" should read -- 1 g --; line 51, "3,89%H," should read -- 3.89%H, --.

Signed and Sealed this

Second Day of November 1982

[SEAL]

Attest:

GERALD J. MOSSINGHOFF

Attesting Officer  Commissioner of Patents and Trademarks